United States Patent [19]
Jubran

[11] Patent Number: 5,204,311
[45] Date of Patent: Apr. 20, 1993

[54] ETHANEDIIMIDIC ACID BIS[(ARYLALKYLIDENE)HYDRAZIDE] COLOR-FORMERS

[75] Inventor: Nusrallah Jubran, St. Paul, Minn.

[73] Assignee: Minnesota Mining and Manufacturing Company, St. Paul, Minn.

[21] Appl. No.: 749,173

[22] Filed: Aug. 23, 1991

[51] Int. Cl.$^5$ .................... B41M 5/132; B41M 5/165
[52] U.S. Cl. ............................... 503/201; 106/21 R; 428/402.2; 503/215; 503/217; 503/225
[58] Field of Search .......... 106/21; 428/402.2, 402.21, 428/402.22; 503/201, 215, 216, 217, 225

[56] References Cited

U.S. PATENT DOCUMENTS

| | | | |
|---|---|---|---|
| 2,551,786 | 5/1951 | Biswell | 252/42.4 |
| 3,481,759 | 12/1969 | Ostlie | 117/36.2 |
| 3,516,941 | 6/1970 | Matson | 252/316 |
| 4,111,462 | 9/1978 | Lange et al. | 106/21 |
| 4,151,201 | 4/1979 | Casnati et al. | 260/600 |
| 4,334,015 | 6/1982 | Yarian | 106/21 |

OTHER PUBLICATIONS

Polymer Preparation, Am. Chem. Soc., Hergenrother, P. M., 1974, Div. Polymer Chemistry, "Polyphenyl-as-triazines and Polyphenylquinoxalines": New and Crosslinked Polymers, pp. 781–786.
Journal of Fluorine Chemistry, Hergenrother, P. M., 1978 "Synthesis of Fluorinated OC-Diketones and AS-Triazines and Quinoxalines", pp. 439–461.
Polymer Letters, vol. 4, 1966, pp. 869–873.
Chem. Ber., 101, 29–34 (1968), Pyl, Seidl and Beyer.
Uber Oxalhydrazidin Und Einige Heterozyklische Ringkomplexe, G. Dedichen, 1936, pp. 1–42.

*Primary Examiner*—Pamela R. Schwartz
*Attorney, Agent, or Firm*—Gary L. Griswold; Walter N. Kirn; Mark A. Litman

[57] ABSTRACT

This invention relates to improved imaging systems based on the formation of yellow colored coordination compounds of transition metals with certain ligands. The formation of colored coordination compounds can be employed to generate images and is important in the manufacture and use of pressure sensitive transfer papers for preparing carbonless copies. In particular, this invention relates to certain ethanediimidic acid bis[(arylalkylidene)hydrazide] compounds, and particularly to certain ethanediimidic acid bis[(o-hydroxyarylalkylidene)hydrazide] compounds, to their coordination compounds with certain transition metals, and to their use in pressure sensitive carbonless copy paper systems. These compounds have been found to provide excellent yellow colors when used in pressure sensitive carbonless copy-papers wherein the image is formed by the reaction of a color-forming compound with transition metal salts such as those of nickel, cobalt, iron, copper, and similar materials. These yellow color-formers have the advantage of greater solubility in encapsulation solvents and lower volatility than previously used yellow color-formers.

The invention also concerns the admixture of these certain color-formers with N-(monosubstituted)dithiooxamides and/or N,N'-(disubstituted)dithiooxamides to form images of various colors and preferably black images during the application of appropriate pressure to pressure sensitive imaging constructions such as carbonless paper constructions.

19 Claims, 1 Drawing Sheet

ETHANEDIIMIDIC ACID BIS[(ARYLALKYLIDENE)HYDRAZIDE] COLOR-FORMERS

BACKGROUND OF THE INVENTION

1. Field of Invention

This invention relates to certain ethane diimidic acid bis[(arylalkylidene)hydrazide compounds, and particularly to certain ethanediimidic acid bis[(o-hydroxyarylalkylidene)hydrazide] color-formers, to their reactions with metal salts to form colored coordination compounds, and to imaging systems based thereon. The formation of colored coordination compounds can be employed to generate images and is important in the manufacture and use of pressure-sensitive transfer papers for preparing carbonless copies.

The invention also concerns the admixture of these certain color-formers with N-(monosubstituted)dithiooxamides and/or N,N'-(disubstituted)dithiooxamides to form images of various colors and preferably black images during the application of appropriate pressure to pressure sensitive imaging constructions such as carbonless paper constructions.

2. Background of the Art

The use of coordination compounds to form imaging sheets has been important in the field of pressure sensitive transfer papers useful for preparing carbonless copies. The present invention provides color-forming compositions which, when complexed with transition metal ions, can provide compositions that exhibit light absorption characteristics such that they appear as intensely yellow colored complexes. This is accomplished in the present invention by the use of certain colorless ethanediimidic acid bis[(arylalkylidene)hydrazide] compounds, and particularly to certain bis[(o-hydroxy arylalkylidene)hydrazide] compounds which provide an intense yellow color when individually complexed with cations of certain transition metals as, for example, nickel$^{2+}$.

The ethanediimidic acid bis[(arylalkylidene)hydrazide] color-forming compounds which are useful in the present invention and are capable of forming colored complexes with transition metal salts can be represented by the following formula, I, as follows;

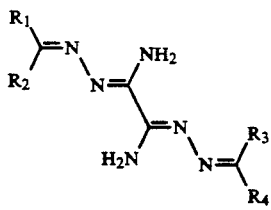

I wherein R$_1$ is selected from the group of substituents comprising an aryl group; particularly phenyl, substituted phenyl, naphthyl, and substituted naphthyl; and most particularly is selected from the group of aromatic substituents consisting of phenyl, substituted phenyl, naphthyl and substituted naphthyl containing an hydroxy group adjacent (i.e., ortho) or pseudo adjacent (i.e., peri) to the site of attachment of the carbon atom attached by a double bond to the nitrogen atom; and R$_2$, R$_3$, and R$_4$, are substituents independently selected from the group of substituents consisting of hydrogen, alkyl group, aryl, substituted aryl, and R$_1$.

The invention also includes within its scope, new ethanediimidic acid bis[(o-hydroxyarylalkylidene)hydrazide] compounds and derivatives of these compounds whereby alkyl groups are substituted on the o-hydroxysubstituted aromatic rings. These new compounds are very soluble in the solvents favored in the encapsulation processes employed in carbonless imaging constructions and the preferred compounds are also low in volatility. When these bishydrazides react with certain metal salts, and especially with nickel salts, strongly yellow-colored coordination complexes are formed. The invention also includes within its scope new coordination complexes of ethanediimidic acid bis[(o-hydroxyarylalkylidene)hydrazide] compounds with various transition metals such as Ni$^{2+}$.

The ligands of the present invention are derivatives of the parent compound, variously known as, oxalimidic acid dihydrazide, oxamide dihydrazone, imidic dihydrazide, oxalimidrazone, and ethanediimidic acid dihydrazide. Chemical Abstracts 11th Collective Index prefers the name ethanediimidic acid dihydrazide. The Chemical Abstracts Registry Number for this compound is [3457-37-2]. The reaction of ethanediimidic acid dihydrazide with aldehydes and ketones forms compounds named as ethanediimidic acid bis[hydrazides]. For example, condensation of 2 molecules of benzaldehyde with one molecule of ethanediimidic acid dihydrazide affords ethanediimidic acid bis[(phenylmethylene)hydrazide]. The Chemical Abstracts Registry number for this compound is [6642-48-4]. This compound can also be named as ethanediimidic acid bis[-(benzylidene)hydrazide]. Herein we refer to compounds derived from the condensation of aromatic aldehydes and ketones with ethanediimidic acid dihydrazide as ethanediimidic acid bis[(arylalkylidene)hydrazide] compounds. Similarly, compounds derived from the condensation between aliphatic aldehydes and ketones with ethanediimidic acid dihydrazide are referred to as ethanediimidic acid bis[(alkylidene)hydrazides].

Condensation of the parent compound with compounds containing two ketone or two aldehyde groups to form polymers has been reported (see P. M. Hergenrother, *Polym. Prepr., Am. Chem. Soc., Div. Polym. Chem.* 974, 781) as has their use in the formation of polymers containing heterocyclic compounds (see P. M. Hergenrother; M Hudlicky, *J. Fluorine Chem.* 1978, 12, 439). Condensation with dicarboxylic acid chlorides to form polymers has also been reported (see M. Saga; T. Shono, *J. Polym. Sci., Part B* 1966, 4, 869).

In contrast to its use in the preparation of polymers, the reaction of ethanediimidic acid dihydrazide with simple aldehydes and ketones has been less studied. The reactions of the this dihydrazide with various aldehydes and ketones was investigated by Dedichen (see G. Dedichen, *Avhandl. Norske Videnskaps-Akad. Oslo, I, Mat.-Naturv. Klasse* 936, No. 5; Chem. Abstr. 1937. 31, 4985[3]). Although the author investigated the coordination chemistry of ethanediimidic acid dihydrazide with metals such as copper, mercury, lead, bismuth, and nickel, no discussion of the coordination of aldehyde and ketone condensation products with metals is given. More recently, Pyl and coworkers prepared a series of ethanediimidic acid bis[(α-(chloromethyl)aryl)methylene] hydrazide compounds (see T. Pyl; L. Seidl; H. Beyer *Chem. Ber.* 1968, 101, 29). They also did not report on the coordination of these compounds with metals. Biswell found that ethanediimidic acid bis[(o-hydroxyarylalkylidene)hydrazide] ligands were useful as stabilizers for fats, drying oils, rubbers, and other synthetic unsaturated substances subject to deterioration by the action of oxygen in the presence of transition metal ions such as $Cu^{2+}$ and $Co^{2+}$. These ligands served to decrease the metal's ability to catalyze oxidation by forming complexes with the metal ion. A structure for the metal complex was proposed. See C. B. Biswell, U.S. Pat. No. 2,551,786 (1951).

In none of the above cited literature have the ligands or coordination compounds been used in any imaging process, nor has any reference to imaging been made, nor has any mention of the requirements of encapsulation been disclosed, nor has any mention been made of the colors the these complexes.

In order to be useful in one embodiment of an imaging construction, it is desirable that the ligand be capable of being encapsulated and of rapidly forming a stable colored image upon contact with a metal cation on a receptor sheet. That is, the transition metal complex should form nearly instantaneously, so that the image is rapidly formed as the stylus pressure is applied to the backside of the donor sheet. This will help ensure formation of an accurate, almost instantly readable copy. The image should also be relatively stable so that it does not substantially fade with time.

One type of carbonless imaging chemistry takes advantage of the fact that dithiooxamide compounds are encapsulable and react readily with many transition metal salts to form coordination complexes. The chemistry and characteristics of certain dithiooxamide materials have been used successfully in commercially available carbonless paper products. Generally, these dithiooxamide compounds comprise symmetrically disubstituted dithiooxamide compounds and include N,N'-dibenzyldithiooxamide and N,N'-di(2-octanoyloxyethyl)dithiooxamide.

Transition metal salts used to form coordination complexes with dithiooxamides which have been employed in the preparation of carbonless image transfer products or constructions are generally those comprising cations having a +2 valance state. Compounds with nickel, zinc, palladium, platinum, copper and cobalt all form such complexes with dithiooxamides. Many of these coordination complexes are deeply colored.

Carbonless imaging constructions, or products employing this chemistry, generally involve placement of one reactant (i.e., one of the transition metal or ligand) on one substrate (for example, sheet of paper) and the other reactant (the one of transition metal or ligand not used on the first substrate) on a second, i.e., mating, substrate. The ligand and metal are maintained separated from contact and reaction with one another. This is typically accomplished by encapsulation of one of the reactants. Herein, the terms "encapsulation" and "encapsulated compounds" refer to microcapsules enclosing a fill material therewithin.

Once rupturing pressure is applied to the construction, as from a stylus or business-machine key, the solution of encapsulated reactant is released, and a complex between the previously separated reactants is formed. In general, the resulting complex will, of course, form a colored image corresponding to the path traveled by the stylus, or the pattern of pressure provided by the key.

In one commercial product, the capsules on a first sheet (donor sheet) contain dithiooxamide (DTO) derivatives, and the mating sheet, sometimes referred to as the receptor sheet, contains a coating of selected salts of nickel. The encapsulated dithiooxamide ligands, in a suitable binder, are coated onto one face of the donor sheet; and, the metal salt, optionally in a suitable binder, is coated onto one face of the receptor sheet. Herein, the term "suitable binder" refers to a material, such as starch, polymer, or latex, that allows for dispersion of the reactants in a coating on a substrate, promotes adhesion of the capsules to the substrate, and permits the capsules to be ruptured under hand-held stylus pressure, or typical business machine key pressure. When the two coated faces are contacted such that the ligands and the metal salt can combine and react, a coordination complex forms and an image results. Typically, this occurs by transfer of the ligand to the site of the metal salt, i.e., transfer of the ligand from the donor sheet to the receptor sheet. The image, of course, forms on the receptor sheet.

In a preferred orientation, the encapsulated ligands, in a suitable binder, are coated on the back of the donor sheet, sometimes referred to as a coated back (CB) sheet, and the metal salt, optionally in a suitable binder, is coated on the front of the receptor sheet, or coated front (CF) sheet. Again, in imaging, the two sheets are positioned such that the encapsulated ligands on the donor (CB) sheet faces the metal salt coating on the receptor (CF) sheet. When pressure is applied to the uncoated surface of the donor sheet, (i.e., the face not in contact with the receptor (CF) sheet), selected capsules rupture (i.e., those capsules corresponding to the pattern of applied pressure) with release of the ligand for transfer to the receptor sheet, forming a colored pattern due to complexation with the salt. In many applications the uncoated surface of the donor (CB) sheet comprises a form of some type. The stylus pressure is generated by means of a pen or other writing instrument used in filling out the form. Thus, the image appearing on the receptor (CF) sheet is a copy of the image applied to the top sheet.

In some applications, multiple form sets have been used. These contain intermediate sheets having a metal salt coating on one side and a coating with capsules of ligand on the opposite side. Such sheets are generally referred to herein as "CFB" sheets (i.e., coated front and back sheets).

Due to the stoichiometry of the system (i.e., the metal salt is usually in excess since relatively little ligand is released), it is generally believed that the image formed on the receptor sheet, after stylus pressure is applied to break the capsules and release the ligand, results from the formation of a complex between one molecule of color-forming ligand and 1 or 2 atoms of a metal having a +2 valence (as for example $Ni^{2+}$). The counterion of the positively charged transition metal is usually the conjugate base of a weak acid and may facilitate removal of the two protons from the color-forming ligands, necessary for complexation with the $M^{2+}$ cation.

In commercial applications, generally, nickel salts have been preferred as the transition metal salts. One reason for this is that nickel salts form a deep color when complexed with the dithiooxamide ligands. The nickel salts are also substantially colorless, and thus do not alone impart color to the receptor (CF) sheet. A third reason is that nickel salts are relatively low in cost, by comparison to other transition metal salts that can be easily and safely handled and that form highly colored coordination complexes with dithiooxamides.

In some applications it is also desirable that the color of the complex be a deep, strong color that is not only pleasing to the eye, but that will exhibit good contrast with the paper, for purposes of later reading and/or photocopying. This has been one drawback with conventional carbonless paper arrangements, which use nickel salts complexed with disubstituted dithiooxamide ligands. The image imparted by the resulting coordination compound, under such circumstances, is generally magenta. The more "red" character the polymer complex exhibits, generally, the less contrasting and pleasing is the appearance. A dark, i.e., preferably black, blue, or blue-black, arrangement would be preferred, but previously such has not been satisfactorily obtainable. Recently, an attempt to achieve a blue or blue-black image by employing encapsulated N-(monosubstituted)dithiooxamides compatible with the transition metal chemistry described above was described (see U.S. Pat. No. 5,124,308). Preparation of these N-(monosubstituted)dithiooxamides is described in U.S. Pat. No. 5,041,654 which is incorporated herein by reference for the disclosure and synthesis of these N-(monosubstituted) dithiooxamides. These may be used either alone or in admixture with N,N'-(disubstituted)-dithiooxamides and can result in a cyan, blue, or blue-black image. A neutral black image would be preferred but has still not been satisfactorily obtainable.

One attempt to prepare a neutral black image using metal coordination chemistry of this type was provided by Yarian. See D. R. Yarian, U.S. Pat. No. 4,334,015 (1982). He found that the combination of certain aromatic-substituted hydrazones with dithiooxamides followed by encapsulation of the mixture provides a method of achieving a dark image. These hydrazones react with the metal on the receiving sheet to form intense yellow images. The yellow coordination compound thus formed, combined with the blue-purple image formed by the dithiooxamide (such as N,N'-di(2-octanoyloxyethyl)dithiooxamide and/or N,N'-dibenzyldithiooxamide), results in an image that appears almost black to the observer.

Although this is a successful approach, Yarian's use of hydrazones still suffers from several drawbacks. The solubility of the hydrazones is not as great in the solvents generally used in the encapsulation process as are dithiooxamides. In addition, the initial image color of the coordination compound formed with N,N'-(disubstituted)dithiooxamide is brown and only after some time does the blue-black to black final image color form. Although much better than the blue-purple coordination compound formed with the N,N'-(disubstituted)dithiooxamide, this mixture of yellow and blue-purple is a dark blue-black rather than the preferred neutral black.

Yarian also noted that the color of capsules prepared from hydrazone compounds was pH dependent and their color may change from essentially colorless at low pH to yellow at pH greater than 9.5 to 10. Yarian further noted that this color change is rapid and reversible upon lowering of the pH. Papers can be divided into classes depending upon their methods of manufacture, treatment and sizing. Among these classifications are acidic and alkaline papers. Encapsulated hydrazones when coated onto "alkaline paper" can form yellow colors.

The ligands generally useful in carbonless paper constructions should also be relatively nonvolatile, so that free ligand, which would result from any inadvertently ruptured capsule, does not readily transfer from the donor sheet to the receptor sheet and form undesired spots of imaged area. That is, so that without the specific assistance of stylus or key pressure, transfer is not readily obtained.

In conventional impact imaging constructions, the capsules can be inadvertently ruptured in steps such as processing, printing, cutting, packaging, handling, storing, and copying. In these situations inadvertent marking or discoloration (i.e., backgrounding) of the sheets results due to inadvertent capsule rupture and transfer of the encapsulated material to the mating sheet where color formation occurs. The amount of inadvertent backgrounding has been reduced in such products by the use of a color control coreactant distributed externally among the capsules. This coreactant is capable of reacting with the contents of the ruptured capsules before transfer of said contents to the receptor sheet and formation of an undesired image. See D. A. Ostlie, U.S. Pat. No. 3,481,759 (1969). Ostlie discovered that addition of a small amount of a metal salt such as a zinc salt to the capsule coating prevents the formation of colored background. The zinc metal ion reacts with the accidently released dithiooxamide compound to form colorless coordination compounds and thus deactivates adventitiously released dithiooxamide materials.

The use of Yarian's invention in combination with that of Ostlie is not possible as zinc forms yellow coordination complexes with the hydrazones of Yarian's invention. Thus, yellow color backgrounding still occurs on the backside of the sheet due to inadvertently ruptured capsules. It would be desireable to have a yellow color-former that could be successfully deactivated by the same method as that described by Ostlie's discovery. Then, the same method of deactivation of the yellow, magenta, and cyan color-formers released by inadvertent capsule rupture would be possible.

Another approach to formation of a black image employs an encapsulated mixture of an acid sensitive green-forming leuco dye and a dithiooxamide color-former. The receptor sheet is formulated to contain phenolic type acids in addition to the transition metal salts. In this system, pressure imaging results in the release of both acid sensitive leuco dyes and dithiooxamide materials. The nickel salt in the receptor sheet reacts with the dithiooxamide to form a purple color and the phenolic acid in the receptor sheet reacts with the acid-sensitive leuco to form a green color. Together they generate a black image. This approach, while successful, has several disadvantages. Heavy coatings to the papers are required as two separate chemistries are involved. Another drawback of this approach is that the rates of reaction for the two chemistries are different and must be balanced by adjustment of the ratios of the two chemistries in the paper construction.

It is also preferred that the ligands should be colorless, since the ligands are often encapsulated and coated onto the backside of a sheet, such as a form, which has printing on one or both sides thereof. This allows for good legibility of printing on the back side of the carbonless copy-paper sheets. This aspect is particularly important if the donor sheet comprises a top sheet for a stack of carbonless papers. Such sheets are often white, so that they can be readily identified as originals, can be readily photocopied, and can be easily read. The presence of color in the coating on the back side of this sheet would detract from the white colored "original" appearance and could make photocopying of this sheet troublesome.

While the above-described preferred characteristics have long been desirable, they have not been satisfactorily achieved with conventional reactants and conventional constructions. What has been needed has been suitable materials and arrangements for achieving the desired features described.

SUMMARY OF THE INVENTION

In part, certain embodiments of the present invention developed from the observation that certain organic compounds are colorless and form yellow complexes upon coordination with certain transition metal ions such as nickel$^{2+}$. When such color-formers are employed in applications such as image transfer constructions (i.e., carbonless paper), a yellow image is produced. When such color-formers are mixed with other compounds capable of forming magenta and cyan colored complexes, a black complex can form upon coordination of this mixture with transition metals.

It is one aspect of this invention to describe color-forming ligands and compositions useful in encapsulated imaging systems wherein the color is formed by formation of a complex between a transition metal cation and a yellow color-former. This is accomplished in the present invention by the use of certain ethanediimidic acid bis[(arylalkylidene)hydrazide] compounds and most preferably to certain ethanediimidic acid bis[(o-hydroxyaryalkylidene)hydrazide] compounds which provide a yellow color when individually complexed with nickel$^{2+}$.

The ethanediimidic acid bis[(arylalkylidene)hydrazide] color-forming compounds which are useful in the present invention and are capable of forming colored complexes with transition metal salts can be represented by the following formula, I, as follows:

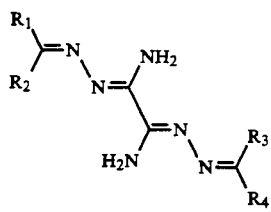

wherein $R_1$ is selected from the group of substituents comprising aryl group; (and particularly phenyl, substituted phenyl, naphthyl, and substituted naphthyl) and alkoxyacetyl (preferably C1 to C8 alkoxy); and most particularly is selected from the group of aromatic substituents consisting of phenyl group, and naphthyl group containing an hydroxy group adjacent (i.e., ortho) or pseudo adjacent (i.e., peri) to the site of attachment of the carbon atom attached by a double bond to the nitrogen atom; and $R_2$, $R_3$, and $R_4$, are substituents independently selected from the group of substituents consisting of hydrogen, alkyl group, aryl group, and $R_1$.

When the term "group" is used to describe a chemical compound or subtituent, the described chemical material includes the basic group and that group with conventional substitution. Where the term "moiety" is used to describe a chemical compound or substituent only an unsubstituted chemical material is intended to be included. For example, "alkyl group" includes not only such alkyl moieties as methyl, ethyl, octyl, stearyl, etc., but also such moieties bearing substituent groups such as halogen, cyano, hydroxyl, nitro, amine, carboxylate, etc. On the other hand, "alkyl moiety" includes only methyl, ethyl, octyl, stearyl, cyanohexyl, etc.

It is another aspect of this invention to teach the preparation of colored coordination compounds of transition metals with the ligands comprised of these ethanediimidic acid bis[(arylalkylidene)hydrazide] compounds.

It is also an aspect of this invention to describe yellow color-formers useful as imaging compositions wherein a mixture of color-formers is employed and the color is formed by the formation of a complex between a transition metal cation and the mixture of color-formers.

It is a further aspect of this invention to demonstrate that yellow color-forming compounds of the type described above can be encapsulated and utilized to form carbonless copy papers that provide strong yellow images. When a mixture of color-formers is encapsulated, images of varying colors can be formed by the formation of a complex between a transition metal cation and the encapsulated color-formers. In particular, when mixed with cyan and magenta color-formers, black images are formed upon imaging.

It is an additional aspect of this invention to show that, the above-identified representative compounds satisfy the requirements of solubility in suitable solvents for encapsulation, non-solubility in aqueous media, non-reactivity with fill solvents and color-formers mixed therewith, compatibility with existing transition metal/dithiooxamide imaging systems, and low volatility at room temperature, i.e., about 25° C. In addition, they are generally colorless to lightly colored color-formers, and impart little or no color to the sheets upon which they are coated in use. Finally, they form generally yellow colors on coordination with at least some transition metal ions, such as nickel.

The most preferred compounds satisfy all the above requirements, plus they are generally nonvolatile at elevated temperatures, i.e., above about 25° C., most preferably above about 49° C. The most preferred compounds include: ethanediimidic acid bis[(o-hydroxyarylalkylidene)hydrazide] derivatives as for example ethanediimidic acid bis[(salicylidene)hydrazide] and substituted versions thereof. That these materials are the most preferred will be apparent from the experiments as reported herein below.

The invention further includes within its scope the provision of a carbonless transfer system or construction utilizing material according to formula I above, as a reactant. In a preferred embodiment, the construction comprises: a donor sheet having encapsulated color-forming ligand according to formula I thereon; and, a receptor sheet having a coating of transition metal salt, preferably a Ni$^{2+}$ salt, thereon. The encapsulation provides means inhibiting reaction between the ligand and the transition metal cation, until appropriate activating pressure is applied to the arrangement.

It will be understood that in some instances the encapsulated color-formers may comprise, in addition to the yellow color-former of formula I, a mixture of an N-(monosubstituted)dithiooxamide (capable of forming blue or cyan image on coordination) and an N,N'-(disubstituted)dithiooxamide (capable of forming magenta or purple color). Should this latter be the case, a generally dark overall color would result upon image formation, provided, however, that an effective amount (i.e., an amount effective to produce a dark black image rather than a yellow image) of dithiooxamide color-formers were also present.

It will also be understood that in some instances the carbonless transfer system may comprise a mixture of capsules, each containing separate encapsulated color-forming ligand solution. In this instance, color would be formed by the mixing of the color-formers upon capsule rupture and reaction with the metal cation. Again, the use of a mixture of capsules each individually containing yellow, magenta or cyan color-former would result in a black color upon image formation, provided, however, that an effective amount (i.e., an amount effective to produce a dark black image rather than a yellow image) of dithiooxamide color-formers were also present.

The invention also includes within its scope a method of forming an image on a receptor sheet comprising: providing a receptor sheet having a surface with a transition metal salt coated thereon; and, transferring to the coated surface of the receptor sheet an effective amount of a compound of structure I. The compound can be volatile or nonvolatile; however, in preferred applications, it will be a nonvolatile compound according to formula I.

DETAILED DESCRIPTION OF THE INVENTION

The Yellow Color-former

Figure 1:
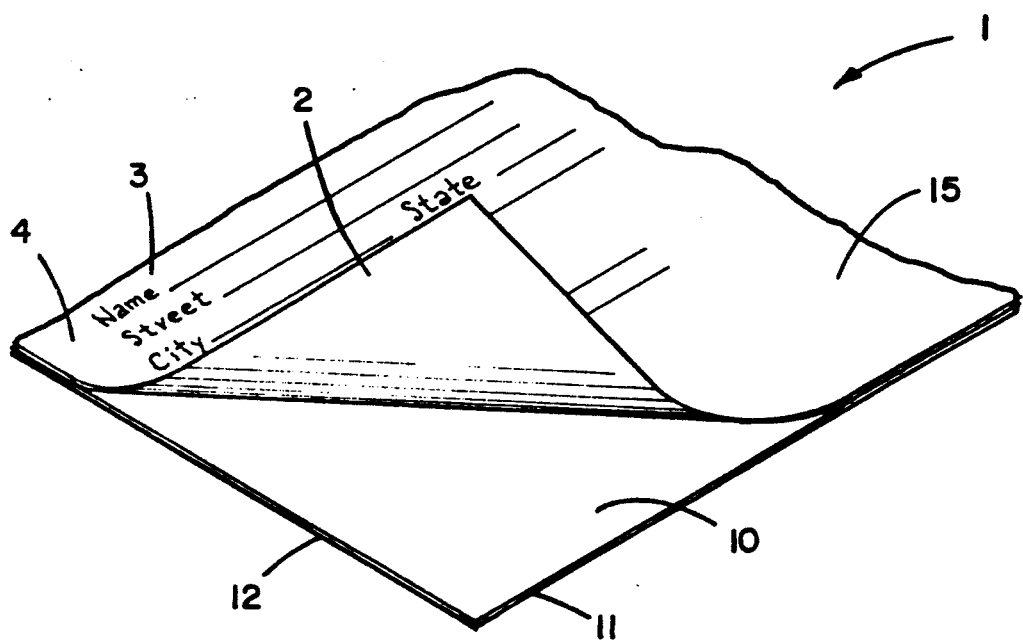
FIGURE 1 is a fragmentary perspective view of a carbonless paper construction according to the present invention, depicted with the first and second substrates thereof partially separated.

Ethanediimidic acid dihydrazide can be prepared in good yield by the reaction of dithiooxamide with hydrazine. The reaction proceeds readily in a 20% alcohol solvent at room temperature and the product separates as a white solid. This solid reacts readily with aldehydes and ketones to form the substituted ethanediimidic acid bis[hydrazide]. Dedichen, vide supra, prepared ethanediimidic acid bis[(benzylidene)hydrazide] (from benzaldehyde and ethanediimidic acid dihydrazide), ethanediimidic acid bis[(salicylidene)hydrazide] (from salicylaldehyde and ethanediimidic acid dihydrazide), ethanediimidic acid bis[(p-anisylidene)hydrazide] (from p-anisaldehyde and ethanediimidic acid dihydrazide), along with other compounds of a similar nature.

We have found that these compounds form yellow coordination compounds with nickel salts, such as nickel 2-ethylhexanoate, nickel rosinate, nickel stearate, nickel benzoate, nickel oleate, nickel hydrocinnamate, nickel 2-phenylbutyrate, nickel calcium rosinate and the like.

In addition to aldehydes, the condensation of the ethanediimidic acid dihydrazide with ketones and particularly with aromatic ketones also leads to compounds which form colored coordination complexes with transition metal salts. Thus, the condensation product of o-hydroxyacetophenone and ethanediimidic acid dihydrazide when reacted with nickel results in a yellow coordination complex.

For the formation of a carbonless paper construction, the preferred condensation products with ethanediimidic acid dihydrazide must be soluble in the solvents used in the encapsulation process. Such aqueous immiscible solvents include xylene, toluene, cyclohexane, diethyl phthalate, tributyl phosphate, and the like. Solubility of ethanediimidic acid bis[(o-hydroxybenzylidene)hydrazide] (i.e., ethanediimidic acid bis[(salicylidene)hydrazide]), for example, is too low in the solvent blend used in many carbonless paper capsules and therefore the color developed upon imaging is weak and often unacceptable. We have found that modifying the structure of the aldehyde or ketone for example by placing alkyl groups onto the aromatic ring, improves the solubility without reducing imaging speed or color. Thus, the condensation of ethanediimidic acid dihydrazide with 3,5-di-t-butylsalicylaldehyde to form ethanediimidic acid bis[(3,5-di-t-butylsalicylidene)hydrazide] (compound 1 below) results in a compound that is very soluble in encapsulation solvents. Likewise, the condensation product between ethanediimidic acid dihydrazide and 3-allylsalicylaldehyde also results in a ligand (compound 16 below) with good solubility in capsule solvents. Preferred substituents on the aromatic ring contain alkyl groups or alkenyl groups of from 1-10 carbon atoms substituted on the ring and an hydroxyl group ortho to the aldehyde or ketone. Several of the preferred compounds of this invention are themselves new compounds, never having been described before.

Aliphatic aldehydes also condense with the imidic dihydrazide to form soluble products, however their coordination product with nickel is weakly colored and is less suitable for imaging chemistry. This is evidenced by compound 15, prepared from 1-heptylaldehyde. When complexed with nickel the coordination compound formed is very weakly yellow and the measured reflectance density and Chroma are low.

As mentioned above, in order to be useful in an encapsulated imaging system, the color-forming ligand must satisfy several requirements. It must be encapsulable and therefore not be soluble in water. It must have low volatility so that the free ligand resulting from inadvertently ruptured capsules does not transfer from the CB to the adjacent CF sheet and form spots of imaged area. It must have low coloration in the uncomplexed state and it must form a stable colored image upon contact with the metal from the CF sheet.

The encapsulation process requires the color-forming ligand be dissolved in a solvent or mixed solvents, because of the nature of the procedure. Formation of a microcapsule shell as by condensation of urea or melamine with an aldehyde such as formaldehyde or mixtures of aldehydes to form the capsule shell is carried out in an acidic aqueous medium and the color-former solution must be insoluble and unreactive to these reagents for the encapsulation to proceed. Solvents commonly used include tributyl phosphate, diethyl phthalate, and cyclohexane. It is apparent that the imaging sheet production depends upon success in this encapsulation and hence upon having suitable solubility of the color-forming ligand in the solvents. As mentioned above, solubility of yellow color-formers exemplified by structure I in nonaqueous solvents such as those used in the encapsulation process may be increased by substituting alkyl, aryl, aralkyl, alkenyl, or such groups for the hydrogens on the various positions available in the structure I above. Representative compounds of structure I are shown in Table 1 below.

The color-forming compositions of the present invention can be readily micro-encapsulated by techniques known in the art, for example as described in G. W. Matson, U.S. Pat. No. 3.516,941 (1970). Pressure-sensitive record and/or transfer sheets can be provided as are known in the art.

Compounds according to formula I as defined are generally insoluble in aqueous solution, soluble in aqueous-immiscible solvents in a pH range of about 1 to 9, and thus are readily encapsulatable. Such aqueous-immiscible solvents include xylene, toluene, cyclohexane, diethyl phthalate, tributyl phosphate, and the like. Compounds included within the scope of formula I as defined also generally readily form yellow images upon coordination with at least certain transition metal salts, and most preferably nickel salts.

It is an important feature of the present invention that the liquid employed as the solvent for the encapsulated reactant be a solvent for the coreactant (such as the metal salt) as well, whether the latter is also encapsulated or not. This same solvent then serves as a reaction implementing medium for the two reactants at the time of rupture of the capsules and is commonly referred to as a cosolvent. Examples of cosolvents which fulfill the above mentioned criteria are cyclohexane, tributyl phosphate, diethyl phthalate, toluene, xylenes, 3-heptanone, and the like. The selection of additional suitable cosolvents will be obvious to those skilled in the art.

It is another feature of this invention that the yellow-colorformers are compatible with metal/dithiooxamide imaging chemistry. They are soluble in the same encapsulation solvents as the dithiooxamides. They also do not react with either the dithiooxamides or the encapsulation solvent. This allows one "imaging chemistry" to be used.

When compared with the yellow color-formers described by Yarian, vide supra, the yellow color-formers of the present invention, represented by structure I, form relatively colorless complexes with $Zn^{2+}$ salts. Thus, the use of the color-formers of the present invention in combination with the color control coreactants taught by Ostlie is now possible and the same method of deactivation of the yellow, magenta, and cyan color-formers released by inadvertent capsule rupture can now be used.

The preferred ethanediimidic acid bis[(o-hydroxyarylalkylidene)hydrazide] color-formers of the present invention are more soluble in the solvents generally used in the encapsulation process and are also less sensitive to color change upon adjustment of pH and maintain their essentially colorless nature when encapsulated and coated onto "alkaline paper."

Those compounds that are relatively nonvolatile at temperatures of at least about 49° C., and preferably up to at least about 71° C., are particularly useful in the embodiments of the invention. Again, the term "nonvolatile", when used with respect to the color-formers according to the present invention, is meant to refer to compounds that pass the volatility test outlined herein below. That is, the compounds are classifiable as nonvolatile under the conditions of the test.

A further consideration to the commercial exploitation of the discovery of more favorable color hues in the coordination compounds is the ease of preparation of the compounds exemplified by structure I. The above-described compounds, and related compounds according to the general formula I, are readily obtainable through synthetic methods known in the literature and further described herein.

The Metal Complex

In a typical application, to generate an image on a substrate, the complex is formed by contacting the color-former (or a solution containing the color-former) with a substrate having a coating of transition metal salt thereon. The preferred transition metal salts are those of nickel; however, salts of copper, iron, and other transition metals may, in certain applications, be used within the scope of this invention. Examples of transition metal salts for this application are nickel 2-ethylhexanoate, nickel rosinate, nickel stearate, nickel benzoate, nickel 2-phenylbutyrate, nickel oleate, nickel hydro-cinnamate, nickel calcium rosinate, and the like [see H. E. Lange, U.S. Pat. No. 4,111,462 (1978)]. preferred transition metal salts for use in this invention are nickel rosinate, nickel 2-hexanoate, and mixtures thereof. Again, formation of the complex is evidenced by appearance of a strong yellow color shortly after the imaging impact takes place.

Although the exact nature of the metal complex between the ethanediimidic acid bis[(arylalkylidene)hydrazide and the transition metal is not known, it is believed that the preferred ethanediimidic acid bis[(o-hydroxyarylalkylidene)hydrazide compounds of the present invention have two tridentate portions and thus can coordinate with one or two transition metal ions having a +2 charge. As the preferred transition metal ion, $nickel^{2+}$, prefers to be tetracoordinate, the fourth coordination site may be occupied by the anion of the transition metal salt used in the color-forming reaction process. An example of one possible structure for the coordination complex between $Ni^{2+}$ and ethanediimidic acid bis[salicylidene] hydrazide is shown is structure II below. It will be understood to those skilled in the art that II represents but one tautomer of several that are possible. Biswell, vide supra, shows a somewhat different structure.

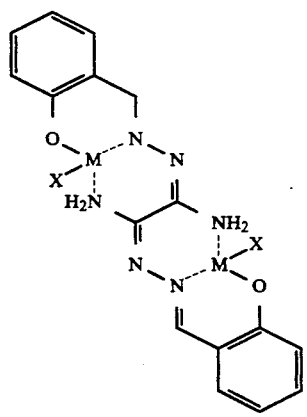

II

The structure of the aldehyde or ketone is also important in the present invention. When aromatic aldehydes or ketones are employed in the condensation reaction with ethanediimidic acid dihydrazide, it is preferred that there should be an electron donating group ortho to the aldehyde group. This provides an additional coordination site for the metal in addition to the nitrogens of the ethanediimide portion of the molecule and enhances the color. Suitable groups include hydroxyl, alkyl ether, thiol, thioether, amine, substituted amine, and similar substituents. Hydroxyl groups are preferred. As demonstrated by compound 2, if an electron donating group is para to the point of substitution of the aldehyde or ketone moiety on the aromatic ring, the colors formed with the transition metal are much weaker (lower Chroma). This is thought to be due to the inability of the transition metal to coordinate with the nitrogens of ethanediimide portion molecule as well as the electron donating group in the para-position of the aromatic group. Aliphatic aldehydes and ketones also condense with ethanediimidic acid dihydrazide to form soluble products, however, their coordination compounds with nickel are weakly colored which is presumed due to the lack of an electron releasing capable of additional coordination with the transition metal. This is evidenced by compound 15, prepared from 1-heptylaldehyde. When complexed with nickel the coordination compound formed is a weak yellow (low Chroma value) and the measured reflectance density is low. The condensation products of heterocyclic aromatic aldehydes and ketones afford ligands of structure I capable of additional coordination through the heteroatom in the pseudo-ortho position. This is exemplified by compounds 12, 13, and 14 in Table 2. The chroma of these compounds is intermediate between that of aliphatic and the preferred o-substituted ligands. Other ligands illustrated in Table 2 demonstrate the role of steric effects in controlling the metal coordination and in controlling the depth of the color formed upon coordination. The colors of various other ethanediimidic acid bis[(arylalkylidene)hydrazides] and ethanediimidic acid bis[(alkylidene)hydrazides] are shown in Table 2. As noted above, the most preferred ligands are those that provide a strong yellow color upon coordination with nickel$^{2+}$ and are also soluble in the solvents useful for encapsulation.

As shown in Experimental Examples 4, 6, and 7 below, when the yellow color-formers of the present invention are used in admixture with certain conventional dithiooxamide derivative transition metal complexing compounds, the light absorption properties of the individual complexes are additive. It is possible to absorb such a substantial portion of light in the visible spectrum so as to providing a neutral, black color. By proper combination of materials additional colors can be formed. For example, a mixture of yellow color-former of this invention with a magenta color-former such as an N,N'-(disubstituted)dithiooxamide will afford a red color upon imaging. This red color can be used in the preparation of carbonless copies of airline tickets. Such copies are usually red. Similarly, a mixture of yellow color-former of this invention with a cyan color-former such as an N-(monosubstituted)dithiooxamide will afford a green image. When a yellow color-former of this invention is mixed with an effective amount of an N-(monosubstituted)dithiooxamide which provides a cyan image and an N,N'-(disubstituted)dithiooxamide which provides a magenta image; or mixtures thereof which provide a dark blue to blue-black image, the resulting complex composition appears black to the observer.

It is noted that complexes formed with the yellow color-formers of the present invention are relatively stable. Further, even if some reversal of coordination does occur, the relatively nonvolatile ethanediimidic acid bis[(arylalkylidene)hydrazide] compounds of this invention will remain on the surface of the receptor sheets, and thus recoordinate.

Carbonless Imaging Constructions

The invention further includes within its scope image transfer systems or constructions, i.e., carbonless impact marking papers for the transfer of images. In general, this involves coating one reactant, the color-former on one substrate, and the transition metal salt (the other reactant) on another, mating, substrate. Means for preventing reaction of the two until intended, i.e., until activating pressure is applied, are also provided. Preferably, the color-forming compounds are contained or encapsulated in microcapsules on one sheet of paper. The reactant for the color-forming compound, i.e., the transition metal salt, is carried on a mating sheet of paper. The microcapsules serve the purpose of isolating the reactants from one another (i.e., preventing reaction) until such time as pressure is applied to the paper for the purpose of creating an image.

Generally, a carbonless paper construction comprises at least two substrates, for example two sheets of paper, each with one surface, or side, coated with one of the two primary reactants. The two substrates are generally referred to as a donor sheet and a receptor sheet. When the coated faces, or surfaces, of the two substrates come into contact under sufficient pressure so that the reactants can mix, a reaction occurs and an image forms on the receptor sheet.

A preferred construction 1 (FIGURE 1) comprises the encapsulated color-forming ligands dissolved in an appropriate solvent(s) within microcapsules and coated onto a back side 2 of a donor sheet 3 in a suitable binder. The back side 2 of donor sheet 3 is sometimes referred to herein as a coated back (CB) sheet 4. The metal salt, preferably a Ni$^{2+}$ salt, optionally in a suitable binder, is coated onto a front side 10 of a mating, or receptor, sheet 11, herein sometimes referred to as a coated front (CF) sheet 12. As stated previously, in imaging, the two sheets are positioned such that the back side 2 of donor sheet 3 faces the metal salt coating on the front side 10 of the receptor sheet 11 as shown in FIGURE 1. When activating pressure is applied to face 15 of the donor sheet 3, the capsules rupture and release the color-forming ligand for transfer to the receptor sheet 11, forming a colored pattern due to complexing with the salt. It is noted that in FIGURE 1 the coated back (CB) sheet 4 and the coated front (CF) sheet 12 are shown partially separated to facilitate understanding of the invention. Herein, "activating pressure" includes, but is not limited to, pressure applied by hand with a stylus or pressure applied by a business machine key, for example a typewriter key.

Also included within the scope of the invention is a construction comprising: a plurality of first substrate surfaces, each on which is coated the encapsulated color-former; and, a plurality of second substrate surfaces, each on which is coated a salt of a transition metal cation with a +2 oxidation state. Each of the coated first substrate surfaces is positioned within the construction in contact with one of the coated second substrate surfaces. Such a construction is known as a form-set construction.

Substrates, with one surface on which is coated the encapsulated color-former, and a second, opposite, surface on which is coated a salt of a transition metal cation (as for example Ni$^{2+}$) can be placed between the CF and CB sheets, in a construction involving a plurality of substrates. Such a sheet is sometimes referred to as a CFB sheet. Of course, each side including color-former thereon should be placed in juxtaposition with a sheet having metal salt thereon. CFB sheets are typically used in form-sets.

The color-forming compounds and compositions of the present invention can be used in the manner that dithiooxamide (DTO) based chemistries have previously been used. Indeed, one advantage of the yellow color-formers of the present invention is their ability to image using the same transition metal coordination chemistry employed in dithiooxamide based imaging systems. For example, pressure sensitive carbonless transfer and record sheets which are capable of providing colored images can be provided by encapsulating the yellow color-forming compounds of the present invention and a cosolvent vehicle in substantially impermeable, pressure-rupturable microcapsules and applying these encapsulated materials to paper substrates. Alternatively, a composition comprising the yellow color-forming compounds of the present invention in a cosolvent vehicle can be carried by a variety of materials such as woven, non-woven or film transfer ribbons for use in impact marking systems such as typewriters and the like, whereby the yellow color-former is transferred to a record surface containing a transition metal salt by impact transfer means. Further, a composition comprising the yellow color-former and a cosolvent vehicle could be absorbed in a porous pad for subsequent transfer to a coreactive record surface by transfer means such as a portion of the human body, e.g. a finger, palm, foot or toe, for providing fingerprints or the like.

Preparation of Substrate (Donor Sheet) Coated with Encapsulated Yellow Color-former A carbonless copy construction comprises a substrate containing microcapsules filled with a compound of formula I dissolved in a suitable fill solvent or solvents, the solution of which is water-insoluble. Preferably, the shell of the capsules are of a water-insoluble urea-formaldehyde product formed by acid-catalyzed polymerization of a urea-formaldehyde precondensate (see G. W. Matson, vide supra, incorporated herein by reference).

A capsule slurry, as prepared from a mixture of the urea-formaldehyde precondensate and a fill material containing yellow color-formers of structure I, is combined with a binding agent, such as aqueous sodium alginate, starch, latex, or mixtures thereof for coating on one face of a substrate. In the preferred embodiment, the back of the donor sheet is coated with the capsule slurry, and is referred to as the coated back (CB) sheet.

Preparation of Substrate (Receptor Sheet) Coated with Metal Salt

The receptor sheet with the transition metal salt coated thereon (also known as the developer sheet) comprises the transition metal salts of organic or inorganic acids. The preferred transition metal salts are those of nickel, although copper, iron, and other transition metals may be used to advantage in some applications.

Inorganic acids that can be used to react with the transition metals to form the transition metal salts are acids whose anions form salts with transition metals and that will dissociate from the transition metal in the presence of the color-forming ligand for the color-forming reaction. Typical inorganic acids are nitric acid and sulfuric acid, which form nickel nitrate and nickel sulfate, respectively.

Organic acids that are useful in forming the transition metal salts, and that readily dissociate in the presence of color-forming ligands, are the aliphatic and aromatic mono- and di- carboxylic acids, substituted aliphatic and aromatic monocarboxylic acids, and heterocyclic monocarboxylic acids. Monocarboxylic aliphatic acids containing about 6 to 20 carbon atoms are preferred. Nickel 2-ethylhexanoate is a particularly preferred color-forming transition metal salt. Other representative transition metal salts are the nickel, iron, and copper salts of the described organic acids. Examples of such are nickel rosinate, nickel calcium rosinate, nickel stearate, nickel 2-phenylbutyrate, nickel oleate, nickel benzoate, and nickel hydro-cinnamate, as well as the copper and iron analogues. Also, included within the scope of the invention are mixtures of these compounds.

The composition including the transition metal salt may be coated on substrates by conventional coating techniques. The transition metal salt is preferably coated on the front side of a substrate, such as a sheet of paper which is referred to as the coated front (CF) sheet. Additionally, the transition metal salt may be formulated into printing compositions and be printed onto all or a portion of a substrate, such as paper (see, for example, H. E. Lange, vide supra).

Evaluation of Volatility

The preferred compounds of the present invention exhibit a preferred volatility level, and are most favored for use in carbonless imaging transfer systems such as the preferred ones described above, in which selected formation of a yellow image is desired. The method utilized in the experiments to both define and evaluate the level of volatility was as follows. A single sheet piece of Grade #10 (20×12 cm) cheesecloth (AF & F., Item No. 588033, American Fiber and Finishing, Inc., Burlington, Mass.) was placed between a simulated donor sheet and a receptor sheet of a carbonless paper construction. The simulated donor sheet comprised a sheet of paper saturated with color-former of structure I, which was used to simulate a CB sheet with ruptured capsules. Pressure was then applied for 24 hours by placing 9 pounds of paper on top of the sheets, to simulate storage conditions of the paper packages. The formation of color on the receptor sheet, due to transfer of volatile color-former thereto, was used as an indication that the particular color-former was less than optimally desirable for carbonless paper constructions, i.e., was volatile. A compound was considered generally to be nonvolatile, within the meaning of the term as used herein to define the present invention and thus to define color-formers most acceptable for use in carbonless image transfer arrangements, if no color was formed after the simulated test was run for about 24 hours at 25° C. In some instances, if no color was formed after storage at room temperature (25° C.), successively higher temperatures were used, as for example 49° C., 60° C., and 71° C. This will be better understood by reference to Experiments 2 and 3 below. In general, the most preferred compounds, with respect to volatility, are those which do not substantially generate color appearance under the conditions of the test, even at the higher temperatures.

Determination of Complex Color

In general, the colors of the complexes, as listed in Table 2 and Experiments 4, 6, and 7 below, were determined by preparing a 1% solution of the color-former or mixture of color-formers in an appropriate solvent. Unless otherwise indicated, the solvent was composed of a mixture of tributyl phosphate (26.5%), diethyl phthalate (17.6%), and cyclohexane (55.9%). The images were formed by applying two stripes of the solution to a substrate coated with a $Ni^{2+}$ coated receptor sheet using a cotton tipped applicator swab. Rapid and complete development of the image was achieved by passing the sheet through a hot shoe adjusted to 102° C., making a revolution every 10 seconds. The visually observed colors were measured and recorded.

One method of color measurement is to determine the color's position in color space. One color space system is the Hunter System; see F. W. Billmeyer, Jr., and M.

Saltzman, *Principles of Color Technology*; John Wiley & Sons; New York, N.Y.; Ch. 2 & 3, 1981. In this system three mutually perpendicular axes (L, a, and b) are needed to define a color. "L" (+z axis) represents the lightness or darkness of the image; "a" (x axis) represents the amount of red or green (+a is red, —a is green); and "b" (y axis) represents the amount of yellow or blue (+b is yellow, —b is blue). By measuring a material's L, a, and b values, the color of one sample can be compared with that of other samples. Another value used in the Hunter System is Chroma (C). Chroma is defined by the equation $[C=(a^2+b^2)^{\frac{1}{2}}]$ and represents the distance of the image coordinates from the origin. The greater the Chroma, the more intense the image. Chroma is used to compare images of the same hue. Because the color of a sample is also dependent upon the color temperature of the illuminating source, the angle at which the sample is illuminated, the angle at which the illumination is reflected, and the angle of the retina illuminated, these all need to be specified. Many instruments have been developed to record these values. One such instrument is the HunterLab LabScan II. This instrument is capable of automatically determining the L, a, and b values for a given sample, and was used for the following examples.

The L, a, and b color coordinates of the more uniform stripe were measured for 45°/0° reflectance on a HunterLab LabScan II, secondary observer, using illuminant C. The observed (image) color and the Hunter coordinates for $Ni^{2+}$ complexes of the yellow color-formers of this invention are given in Table 2.

The observed (image) color and the Hunter coordinates of mixtures of the yellow color-formers of this invention with N-(monosubstituted)dithiooxamides and N,N'-(disubstituted)dithiooxamides are noted in Experiments 4, 6, and 7 below. Magenta and cyan color-formers described in U.S. patent application Ser. No. 07/473,776, now abandoned, have been found to be particularly effective when used in admixture with the yellow color-formers of this invention. Examples of such magenta and cyan color-formers that may be employed are shown below. The compounds shown below are exemplary only and are not to be considered limiting.

|   | Magenta Color-formers |
|---|---|
| A | N,N'-di(2-octanoyloxyethyl)diethiooxamide |
| B | N,N'-di(dodecyl)dithiooxamide |
| C | N,N'-di(2-decanoyloxyethyl)dithiooxamide |
| D | N,N'-di(2-dodecanoyloxyethyl)dithiooxamide |
| E | N,N'-di(2-octanoylamidoethyl)dithiooxamide |
| F | N,N'-di(6-propanoylamidohexyl)dithiooxamide |
| G | N,N'-di(5-octanoylamido-2-methyl-pentyl)-dithiooxamide mixed with N-(5-octanolyamido-2-methylpentyl)-N'-(5-octanoylamido-4-methylpentyl)dithiooxamide and N,N'-di(5-octanolyamido-4-methylpentyl)dithiooxamide |
| H | N,N'-di(benzyl)dithiooxamide |
| I | N,N'-di(benzoyloxyethyl)dithiooxamide |
|   | Cyan Color-formers |
| A' | N-(2-octanoyloxyethyl)dithiooxamide |
| B' | N-dodecyldithiooxamide |
| C' | N-(2-decanoyloxyethyl)dithiooxamide |
| D' | N-(2-dodecanoyloxyethyl)dithiooxamide |
| E' | N-(2-octanoylamidoethyl)dithiooxamide |
| F' | N-(6-propanoylamidohexyl)dithiooxamide |
| G' | N-(5-octanoylamido-2-methylpentyl)dithiooxamide mixed with N-(5-octanolyamido-4-methylpentyl)dithiooxamide |

EXPERIMENTAL EXAMPLES

As the following experiments show, according to the present invention, there is defined a class of color-formers defined by structure I useable in the formation of a yellow complex upon association with a transition metal cation. The complex is not only of the preferred color, but also the class of compounds according to the invention is relatively nonvolatile and thus readily useable in products for which a yellow component of the image is preferred, such as carbonless paper constructions.

Experiment 1

Preparation of Ethanediimidic Acid Dihydrazide

One gram of dithiooxamide (DTO) and 10 ml. of 85% hydrazine were stirred for one hour at room temperature in a 100 ml. beaker. Water was added to bring the total solution to 50 ml and the white precipitate was removed by filtration and dried in air for two days. The yield of ethanediimidic acid dihydrazide was 0.5 grams (40%).

Experiment 2

Condensation of 3,5-Di-t-butylsalicylaldehyde with Ethanediimidic Acid Dihydrazide - Compound 1

Ethanediimidic acid dihydrazide (10.4 g, 0.09 mol) was dissolved in 600 ml of hot 80% ethanol. 3,5-di-t-butylsalicylaldehyde (41.83 g, 0.180 mol) was added and the solution was boiled for 15 minutes. The 3,5-di-t-butylsalicylaldehyde was prepared as described by Casnati [see G. Casnati, et al., U.S. Pat. No. 4,151,201 (1979) incorporated herein by reference]. Stirring for an additional 30 minutes was followed by cooling to room temperature. The volume of solvent was reduced to about half of the original amount, then the solid product was filtered from the mother liquor. After drying at room temperature for 24 hours, the product weighed 45 g (0.082 mol) and represented a 9i% yield.

A 1% solution of the condensation product in the encapsulation fill mix was swabbed onto a carbonless paper CF sheet (sold by the 3M Co. St. Paul, Minn.) with a cotton swab. The reflectance spectra had Hunter coordinates of:

L=79.8 a=—2.1 b=39.3

This color observed on the CF sheet was yellow. The ligand is stable in concentrated hydrochloric acid, thus demonstrating its usefulness in urea-formaldehyde encapsulation processes. It does not form color when reacted with zinc rosinate. Solubility in a solvent blend of tributyl phosphate, diethyl phthalate and cyclohexane (capsule solvents for preparing carbonless copy-paper) was >9% by weight. Thus the ligand is eminently suitable for encapsulation. The ligand is not volatile at 71° C. overnight.

Experiment 3

Condensation of 3-Allylsalicylaldehyde with Ethanediimidic Acid Dihydrazide - Compound 16

Ethanediimidic acid dihydrazide (2.5 g, 0.0043 mol) was dissolved in 100 ml of 80% ethanol. 3-Allyl-salicylaldehyde (1.508 g, 0.0093 mol) was added and the mixture was heated to 70° C. with stirring for 30 min. The 3-allylsalicylaldehyde was purchased from Frinton Laboratories, Vineland, N.J. The solution turned a light yellow color upon addition of the aldehyde. The mixture was cooled to room temperature, the volume of the reaction mixture was reduced to about 50 ml and the light yellow solid was filtered from the liquid. The solid was dried at room temperature for two days. Infra-red spectra corresponded to that expected for ethanediimidic acid bis[(3-allylsalicylidene)hydrazide]. The yield was 1.3 g (75%).

A 1% solution of the condensation product in the encapsulation fill mix was swabbed onto a carbonless paper CF sheet (sold by the 3M Co. St. Paul, Minn.) with a cotton swab. The reflectance spectra had Hunter coordinates of:

$$L=82.5 \; a=-6.64 \; b=41.0$$

This color observed on the CF sheet was yellow. The ligand is stable in concentrated hydrochloric acid, and does not form color when reacted with zinc rosinate.

Solubility in a solvent blend of tributyl phosphate, diethyl phthalate and cyclohexane (capsule solvents for preparing carbonless copy-paper) was 3% by weight. Thus the ligand is eminently suitable for encapsulation. The ligand is not volatile at 71 ° C. overnight.

In a manner similar to that described above, the following ethanediimidic acid bis[(arylalkylidene)hydrazides and ethanediimidic acid bis[(alkylidene)hydrazides] were prepared:

Compound 2: Ethanediimidic acid bis[(4-hydroxy-3,5-di-t-butylphenylmethylene)hydrazide] was prepared form ethanediimidic acid and 4-hydroxy-3,5-di-t-butylbenzaldehyde. The 4-hydroxy-3,5-di-t-butylbenzaldehyde was purchased from Aldrich Chemical Co., Milwaukee, Wis.

Compound 3: Ethanediimidic acid bis[(2-hydroxy-5-bromophenylmethylene)hydrazide] was prepared form ethanediimidic acid and 2-hydroxy-5-bromobenzaldehyde. The 2-hydroxy-5-bromobenzaldehyde was purchased from Aldrich Chemical Company, Milwaukee, Wis.

Compound 4: Ethanediimidic acid bis[(2-hydroxy-5-nitrophenylmethylene)hydrazide] was prepared form ethanediimidic acid and 2-hydroxy-5-nitrobenzaldehyde. The 2-hydroxy-5-nitrobenzaldehyde was purchased from Aldrich Chemical Company, Milwaukee, Wis.

Compound 5: Ethanediimidic acid bis[(2-hydroxy-4-diethylaminophenylmethylene)hydrazide] was prepared form ethanediimidic acid and 2-hydroxy-4-diethylaminobenzaldehyde. The 2-hydroxy-4-diethylaminobenzaldehyde was purchased from Aldrich Chemical Company, Milwaukee, Wis.

Compound 6: Ethanediimidic acid bis[(2-hydroxyphenyl-methyl-methylene)hydrazide] was prepared form ethanediimidic acid and 2-hydroxyacetophenone.

Compound 7: This compound was prepared from ethyl acetoacetate (acetoacetic ester) and ethanediimidic acid dihydrazide.

Compound 8: Ethanediimidic acid bis[(2,4-dihydroxyphenyl-phenyl-methylene)hydrazide] was prepared form ethanediimidic acid and 2,4-dihydroxybenzophenone. 2,4-dihydroxybenzophenone was purchased from Aldrich Chemical Company, Milwaukee, Wis.

Compound 9: Ethanediimidic acid bis[(2-hydroxyphenylmethylene)hydrazide] was prepared form ethanediimidic acid and 2-hydroxybenzaldehyde (salicylaldehyde). The salicylaldehyde was purchased from Eastman Organic Chemicals Division of Eastman Kodak Company, Rochester, N.Y.

Compound 10: Ethanediimidic acid bis[(2-hydroxy-3-methoxyphenylmethylene)hydrazide] was prepared form ethanediimidic acid and 2-hydroxy-3-methoxybenzaldehyde (o-vanillin). o-Vanillin was purchased from Aldrich Chemical Company, Milwaukee, Wis.

Compound 11: Ethanediimidic acid bis[(2-hydroxy-3-ethoxyphenylmethylene)hydrazide] was prepared form ethanediimidic acid and 2-hydroxy-3-ethoxybenzaldehyde. The 2-hydroxy-3-ethoxybenzaldehyde was purchased from Givaudan Corporation, Clifton, N.J.

Compound 12: Ethanediimidic acid bis[(furylmethylene)hydrazide] was prepared form ethanediimidic acid and 2-furaldehyde. The 2-furaldehyde (furfural) was purchased from Aldrich Chemical Company, Milwaukee, Wis.

Compound 13: Ethanediimidic acid bis[(2-thienylmethylene)hydrazide] was prepared form ethanediimidic acid and 2-thiophenecarboxaldehyde. The 2-thiophenecarboxaldehyde was purchased from Aldrich Chemical Company, Milwaukee, Wis.

Compound 14: Ethanediimidic acid bis[(2-pyridylmethylene)hydrazide] was prepared form ethanediimidic acid and 2-pyridenecarboxaldehyde. The 2-pyridinecarboxaldehyde was purchased from Aldrich Chemical Company, Milwaukee, Wis.

Compound 15: Ethanediimidic acid bis[(heptyl)hydrazide] was prepared from ethanediimidic acid and 1-heptylaldehyde.

Compound 17: Ethanediimidic acid bis[(2-hydroxy-1-naphthylmethylene)hydrazide] was prepared form ethanediimidic acid and 2-hydroxy-1-naphthaldehyde. The 2-hydroxy-1-naphthaldehyde was purchased from Aldrich Chemical Company, Milwaukee, Wis.

Experiment 4

Preparation of Black Image

A mixture of 30% by weight of compound (16), 40% N-dodecyldithiooxamide (B'), and 30% N,N'-di(2-octanoyloxyethyl)dithiooxamide (A) was dissolved in tributyl phosphate, diethyl phthalate and cyclohexane (27:28:56 ratio by weight) so that the percent solids was 2%. A cotton swab of the solution was wiped onto a CF sheet and the resulting image had the Hunter coordinates as follows:

$$L=43.6 \; a=-0.45 \; b=0.65$$

The L value indicates the image is dark and has good contrast on a light background. The values of a and b indicate the image is black.

Experiment 5

Encapsulation of Ethanediimidic Acid Bis[(arylalkylidene)hydrazide] Compounds and Preparation of the CB Sheet A precondensate solution was prepared comprising 192 g of formalin, 0.63 g of potassium tetraborate, 72 g of urea, and 328 g of soft water. The formalin was 37% formaldehyde and was added to a 1-liter flask equipped with a stirrer and heating mantle. The potassium tetraborate and urea were then added, and the mixture was heated to 70° C. The reaction was maintained at that temperature for 2.5–3.0 hr. The reaction mixture was then diluted with the water and allowed to cool. The precondensate solution, with about 24% solids, was then ready for use in the encapsulation process.

The precondensate and fill (ethanediimidic acid bis[hydrazide] and carrier or fill solvents) were combined to make capsules according to the following procedure. Sodium chloride (29.54 g) was added to the stirred precondensate solution and the temperature of the solution was adjusted to 20° C. The fill material (215 g) was added and full agitation was begun. After 5 minutes of stirring, 10% hydrochloric acid solution was added over 5 minutes in an amount such that the final pH of the reaction mixture was about 2.8. The reaction mixture was stirred for another 12 minutes. More of the 10% hydrochloric acid solution was added over a period of 12 minutes, in an amount such that the final pH of the solution was about 18. The reaction mixture was stirred at 20° C. for 1 hr, and then at 60° C. for 1-3 hr. The acidic solution was allowed to cool and adjusted to a pH of 7 by addition of concentrated ammonium hydroxide solution (28%). The capsule slurry could then be stored for later use.

The capsule slurry (10 g) was added to 65 g of a 1.5% aqueous sodium alginate solution. The mixture was applied to a coated paper using a bar coater with a 3 mil gap. The coating was allowed to dry at room temperature.

Experiment 6

Formation of Dark Images by Blending of Capsules

A 2% solution of the compound 1 in the capsule fill solvent of diethyl phthalate, tributyl phosphate, and cyclohexane was encapsulated by the procedure described in Experiment 5 above. A coating mixture of 10.0 g of capsule slurry, 2.5 g of Dow-620 butadiene-styrene latex, and 62.5 g of 1.5% sodium alginate slurry was coated onto paper by the draw down procedure described above. The coated sheet was neutral in color and when imaged with a CF sheet coated with a nickel$^{2+}$ salt, an image was formed with Hunter coordinates of:

$L=84.0 \ a=-2.04 \ b=31.0$

The values for a and b indicate the image to be yellow in color.

A 7.5% solution comprising 5.45% N-(5-octanoylamido-2-metylpentyl)dithiooxamide/N-(5-octanoylamido-4-methylpentyl)dithiooxamide (G') mixture and 2.05% N,N'-di(5-octanoylamido-2-methylpentyl)dithiooxamide/N-(5-octanoylamido-2-methylpentyl)-N'-(5-octanoylamido-4-methylpentyl)dithiooxamide/N,N'-(5-octanoylamido-2-methylpentyl)dithiooxamide (G) mixture in the fill solvent mixture of diethyl phthalate, tributyl phosphate, and cyclohexanone was encapsulated by the procedure described above. A coating mixture of 10.0 g of capsule slurry, 2.5 g of Dow 620 styrene-butadiene latex, and 62.5 g of 1.5% sodium alginate solution was coated onto paper by the draw down procedure described in Experiment 5 above. The coated CB sheet was neutral in color and when imaged with a CF sheet coated with a nickel$^{2+}$ salt an image was formed with Hunter coordinates of:

$L=48.7 \ a=-9.09 \ b=-16.9$

The L value indicates the image is dark and has good contrast on a light background. The values for a and b indicate the image is blue in color.

A blend was prepared of 10 g of the capsule slurry containing compound 1, with 10 g of capsule slurry containing 5.45% N-(5-octanoylamido-2-methylpentyl)dithiooxamide/N-(5-octanoylamido-4-methylpentyl)dithiooxamide (G') mixture and 2.05% N,N'-di(5-octanoylamido-2-methylpentyl)dithiooxamide/N-(5-octanoylamido-2-methylpentyl)-N'-(5-octanoylamido-4-methylpentyl)dithiooxamide/N,N'-di(5-octanoylamido-4-methylpentyl)dithiooxamide (G) mixture. A coating mixture of the combined capsule slurries, 2.5 g of Dow-620 styrenebutadiene latex, and 62.5 g of 1.5% sodium alginate solution was coated onto paper using the draw-down procedure described above. The thus formed coated CB sheet was neutral in color. When imaged with a CF sheet coated with a nickel$^{2+}$ salt a black image was formed with Hunter coordinates of:

$L=52.1 \ a=1.26 \ b=-1.24$

The L value indicates the image is dark and has good contrast on a light background. The values of a and b indicate the image is black.

Experiment 7

Encapsulation of Black Image Formulations

A mixture of 30% by weight of compound 1, 50% of N,dodecyldithiooxamide (B'), and 20% N,N'-di(2-octanoyloxyethyl)dithiooxamide (A) was dissolved at a 4% solids level in the capsule solvent blend of diethyl phthalate, tributyl phosphate, and cyclohexane. The solution was encapsulated and coated to form a CB sheet as described in Experiment 5 above. The coated CB sheet was neutral in color. When imaged with a CF sheet, the image appeared a neutral black and had Hunter coordinates of:

$L=56.1 \ a=-1.01 \ b=1.40$

The L value indicates the image is dark and has good contrast on a light background. The values of a and b indicate that the image is a neutral (black) color.

A mixture of 30% by weight of compound 16, 40% by weight of N-dodecyldithiooxamide (B'), and 30% by weight of N,N'-di(2-octanoyloxyethyl)dithiooxamide (A) was dissolved in the fill mix to prepare a solution containing 10% solids. The solution was encapsulated by the procedure described above in Experiment 5. The capsules were coated by this procedure and gave a CB sheet which formed an image with Hunter coordinates of:

$L=43.8 \ a=0.91 \ b=-0.33$

The L value indicates that the image is dark and has good contrast on a light background. The values of a and b indicate that the image is a neutral (black) color.

The invention has been described with reference to various specific and preferred embodiments and techniques. It should be understood, however, that many variations and modifications may be made while remaining within the spirit and scope of the invention.

TABLE 1

Representative Ethanediimidic Acid Bis[hydrazides]

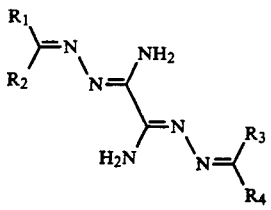

| Reference No. | $R_1$, $R_3$ | $R_2$, $R_4$ |
|---|---|---|
| 1 | 2-hydroxy-3,5-di-t-butylphenyl | H |
| 2 | 4-hydroxy-3,5-di-t-butylphenyl | H |
| 3 | 2-hydroxy-5-bromophenyl | H |
| 4 | 2-hydroxy-5-nitrophenyl | H |
| 5 | 2-hydroxy-4-diethylaminophenyl | H |
| 6 | 2-hydroxyphenyl | $CH_3$ |
| 7 | EtO—C(O)CH$_2$— | $CH_3$ |
| 8 | 2,4-dihydroxyphenyl | phenyl |
| 9 | 2-hydroxyphenyl | H |
| 10 | 2-hydroxy-3-methoxyphenyl | H |
| 11 | 2-hydroxy-3-ethoxyphenyl | H |
| 12 | 2-furyl | H |
| 13 | 2-thienyl | H |
| 14 | 2-pyridyl | H |
| 15 | n-hexyl | H |
| 16 | 2-hydroxy-3-allylphenyl | H |
| 17 | 2-hydroxy-1-naphthyl | H |

TABLE 2

Color Coordinates of Ni(II) Complexes of Yellow-Color-formers

| Ref. No. | *Dye Solubility | Swab Concn. | Image Color | Hunter Coordinates | | | Chroma |
|---|---|---|---|---|---|---|---|
| | | | | L | a | b | |
| 1 | >9.0% | 1% | Yellow | 79.8 | −2.1 | 39.3 | 39.3 |
| 2 | >2.0% | 1% | Light Yellow | 90.0 | −8.0 | 17.6 | 19.2 |
| 3 | <2.0% | 1% | Yellow | 81.9 | −7.5 | 40.5 | 41.1 |
| 4 | <2.0% | 1% | Yellow | 83.9 | −9.7 | 38.9 | 40.1 |
| 5 | <2.0% | 1% | Yellow | 80.9 | −5.2 | 41.0 | 41.4 |
| 6 | <2.0% | 1% | Yellow | 48.3 | −5.3 | 19.4 | 20.1 |
| 7 | >2.0% | 1% | Light Yellow | 89.4 | −5.8 | 14.3 | 15.4 |
| 8 | <2.0% | 1% | Light Green | 88.0 | −6.0 | 17.0 | 18.0 |
| 9 | <2.0% | 1% | Yellow | 84.5 | −9.7 | 39.5 | 40.7 |
| 10 | <2.0% | 1% | Yellow | 86.4 | −11.1 | 34.5 | 36.2 |
| 11 | <2.0% | 1% | Yellow | 88.4 | −15.2 | 36.2 | 39.3 |
| 12 | <2.0% | 1% | Yellow | 89.4 | −10.6 | 23.5 | 25.8 |
| 13 | <2.0% | 1% | Brown | 72.6 | 11.2 | 13.9 | |
| 14 | <2.0% | 1% | Yellow | 86.5 | −11.0 | 33.2 | 35.0 |
| 15 | >2.0% | 1% | Light Yellow | 89.9 | −4.2 | 10.8 | 11.6 |
| 16 | >3.0% | 1% | Yellow | 82.5 | −6.6 | 41.0 | 41.6 |
| 17 | <2.0% | 1% | Yellow | 86.6 | −6.5 | 27.8 | 28.5 |

*THE SOLUBILITY WAS DEEMED PREFERABLE IF IT WAS GREATER THAN 2% IN THE FILL MIX AT ROOM TEMPERATURE FOR 3 DAYS. THE FILL MIX COMPRISED TRIBUTYLPHOSPHATE (26.5%); DIETHYLPHTHALATE (17.6%); AND CYCLOHEXANE (55.9%).

What is claimed and desired to be secured by Letters Patent is as follows:

1. A composition capable of forming colored complexes with transition metal salts, said composition comprising an ethanediimidic acid bis[(arylalkylidene)hydrazide] compound carried in an organic cosolvent vehicle, said compound having the formula:

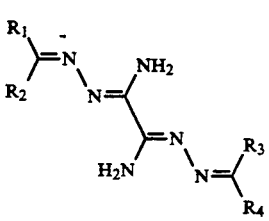

wherein $R_1$ is selected from the group consisting of aryl group and alkoxyacetl group; and $R_2$, $R_3$, and $R_4$, are substituents independently selected from the group of substituents consisting of hydrogen, alkyl group, aryl group and alkoxyacetyl wherein an N-(monosubstituted)dithiooxamide, an N,N'-(disubstituted)dithiooxamide, or a mixture thereof, is also contained in the organic cosolvent.

2. The composition of claim 1 wherein the ethanediimidic acid bis[(arylalkylidene)hydrazide] color-former is represented by the formula:

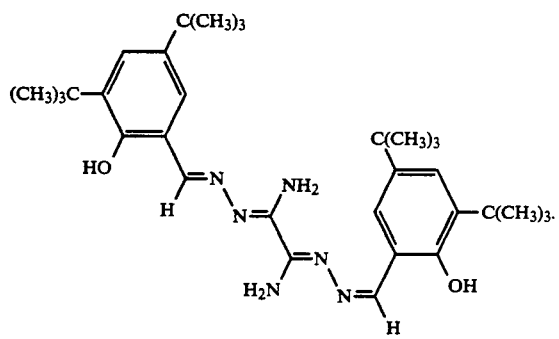

3. The composition of claim 1 wherein the ethanediimidic acid bis[(arylalkylidene)hydrazide] color-former is represented by the formula:

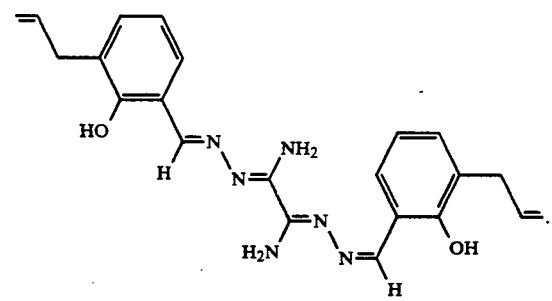

4. A construction comprising:
(a) a first substrate with a surface on which is coated an ethanediimidic acid bis[(arylalkylidene)hydrazide] color-forming compound of the formula:

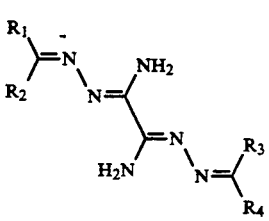

wherein R₁ is selected from the group consisting of an aryl group and an alkoxyacetyl group; and R₂, R₃, and R₄, are substituents independently selected from the group of substituents consisting of hydrogen, alkyl group, aryl group and alkoxyacetyl.
(b) a second substrate with a surface on which is coated a salt of a transition metal cation with a +2 oxidation state, wherein said second substrate surface is juxtaposed in contact with said coated surface of said first substrate; and
(c) means for separating said color-former from reaction with said transition metal cation until said construction is subjected to activating pressure.

5. The construction according to claim 4 wherein the ethanediimidic acid bis[(arylalkylidene)hydrazide] color-former is represented by the formula

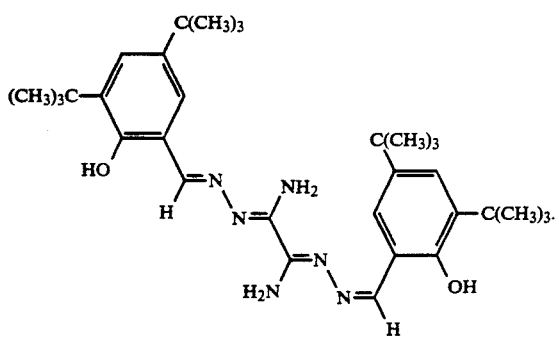

6. The construction according to claim 4 wherein the ethanediimidic acid bis[(arylalkylidene)hydrazide] color-former is represented by the formula:

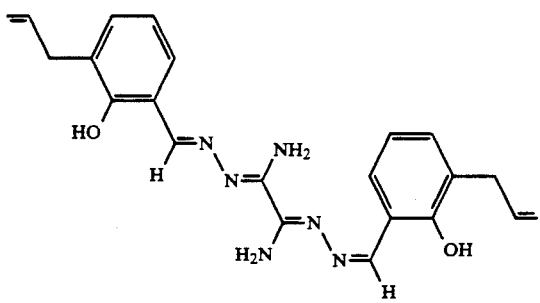

7. The construction according to claim 4 wherein said surface of said first substrate, which is coated with an ethanediimidic acid bis[(arylalkylidene)hydrazide] color-forming compound is also coated with an N-(monosubstituted)dithiooxamide, an N,N'-(disubstituted)dithiooxamide, or a mixture thereof.

8. The construction according to claim 4 wherein said ethanediimidic acid bis[(arylalkylidene)hydrazide] color-former is encapsulated in a substantially impermeable, pressure-rupturable microcapsule.

9. The construction according to claim 8 wherein said surface of said first substrate, which is coated with an encapsulated ethanediimidic acid bis[(arylalkylidene)-hydrazide] color-forming compound is also coated with an encapsulated N-(monosubstituted)dithiooxamide, an N,N'-(disubstituted)dithiooxamide, or a mixture thereof.

10. The construction according to claim 8 wherein said surface of said first substrate, is coated with an encapsulated ethanediimidic acid bis[(arylalkylidene)-hydrazide] mixed with an N-(monosubstituted)dithiooxamide, an N,N'-(disubstituted)dithiooxamide, or a mixture of an N-(monosubstituted)dithiooxamide and an N,N'-(disubstituted)dithiooxamide.

11. The construction according to claim 4 wherein said construction comprises:
(a) a plurality of first surfaces, each of which is coated with the ethanediimidic acid bis[(arylalkylidene)-hydrazide] color-forming compound;
(b) a plurality of second surfaces, each of which is coated with the transition metal salt; and wherein
(c) each of said coated first surfaces is juxtaposed in contact with one each of said coated second surfaces.

12. The construction according to claim 11 wherein said surface of said first substrate, which is coated with an ethanediimidic acid bis[(arylalkylidene)hydrazide] color-forming compound is also coated with an N-(monosubstituted)dithiooxamide, an N,N'-(disubstituted)dithiooxamide, or a mixture thereof.

13. A method of forming an image on a receptor sheet; said method comprising:
(a) providing a receptor sheet comprising a surface with a transition metal salt coated thereon; and
(b) transferring to said coated surface of the receptor sheet an effective amount of an ethanediimidic acid bis[(arylalkylidene)hydrazide] color-forming compound of formula:

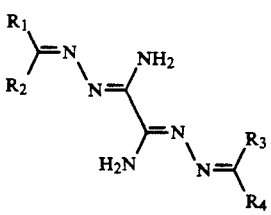

wherein R₁ is selected from the group consisting of an aryl group and an alkoxyacetyl group; and R₂, R₃, and R₄, are substituents independently selected from the group of substituents consisting of hydrogen, alkyl group, aryl group and alkoxyacetyl.

14. The method according to claim 23 wherein said step of transferring comprises:
(a) providing a donor sheet comprising a surface with said color forming compound encapsulated in microcapsules and coated thereon;
(b) placing said coated surface of the donor sheet in contact with said coated surface of the receptor sheet; and
(c) applying activating pressure to said donor sheet sufficient to break the microcapsules and release the encapsulated compound for transfer to said receptor sheet.

15. The method according to claim 13 wherein said step of transferring further comprises transferring an N-(monosubstituted)dithiooxamide compound, an N,N'-(disubstituted)dithiooxamide compound, or a mixture thereof, to the coated surface, along with the effective amount of ethanediimidic acid bis[(arylalkylidene)-hydrazide] compound.

16. The method according to claim 13 wherein said color-forming compound is represented by the formula:

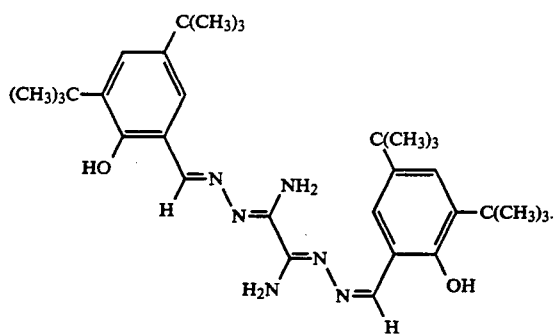

17. The method according to claim 13 wherein said color-forming compound is represented by the formula:

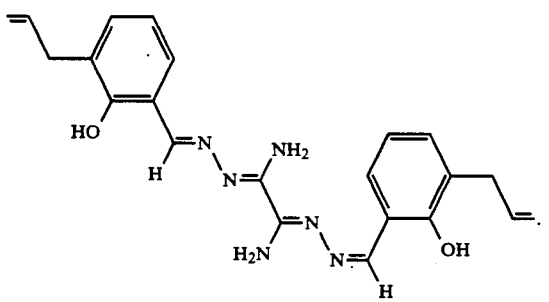

18. A microcapsule containing a composition capable of forming colored complexes with transition metal salts, said composition comprising an ethanediimidic acid bis[(arylalkylidene)hydrazide] compound carried in an organic cosolvent vehicle, said compound having the formula:

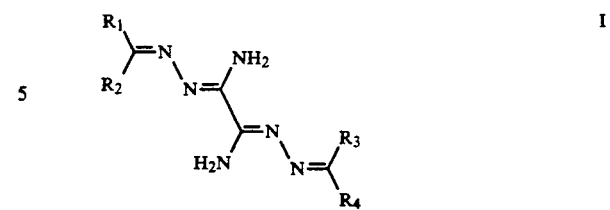

wherein $R_1$ is selected from the group consisting of aryl group and alkoxyacetyl group; and $R_2$, $R_3$, and $R_4$, are substituents independently selected from the group of substituents consisting of hydrogen, alkyl group, aryl group and alkoxyacetyl, and wherein an N-(monosubstituted)dithiooxamide, an N,N'-(disubstituted)dithiooxamide, or a mixture thereof, is also contained in the organic cosolvent vehicle.

19. A composition capable of forming colored complexes with transition metal salts, said composition comprising an ethanediimidic acid bis[(arylalkylidene)hydrazide] compound carried in an organic cosolvent vehicle, said compound having the formula:

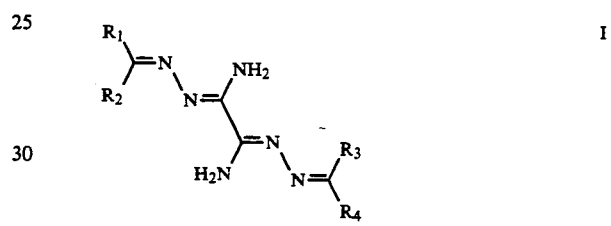

wherein $R_1$ is selected from the group consisting of substituents comprising aryl group and alkoxyacetyl group; and $R_2$, $R_3$, and $R_4$, are substituents independently selected from the group consisting of hydrogen, alkyl group, aryl group and alkoxyacetyl;

wherein an N-(monosubstituted)dithiooxamide, an N,N'-(disubstituted)dithiooxamide, or a mixture thereof, is also contained in the organic cosolvent.

* * * * *

UNITED STATES PATENT AND TRADEMARK OFFICE
CERTIFICATE OF CORRECTION

PATENT NO.  : 5,204,311
DATED       : April 20, 1993
INVENTOR(S) : Jubran

It is certified that error appears in the above-identified patent and that said Letters Patent is hereby corrected as shown below:

| | |
|---|---|
| Col. 2, line 56 | "Klasse 936" should be --Klasse 1936-- |
| Col. 17, line 48 | "diethiooxamide" should be --dithiooxamide-- |
| Col 18, line 39 | "9i% yield" should be 91% yield-- |
| Col. 22, line 12 | "I.5%" should be --1.5%-- |

UNITED STATES PATENT AND TRADEMARK OFFICE
CERTIFICATE OF CORRECTION

PATENT NO. : 5,204,311

DATED : April 20, 1993

INVENTOR(S) : Jubran

It is certified that error appears in the above-indentified patent and that said Letters Patent is hereby corrected as shown below:

Col. 12, line 31

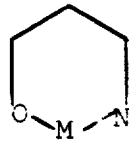

should be

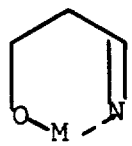

Signed and Sealed this

Fourth Day of October, 1994

Attest:

BRUCE LEHMAN

*Attesting Officer*       *Commissioner of Patents and Trademarks*